(12) United States Patent
Kerselaers et al.

(10) Patent No.: US 10,464,569 B2
(45) Date of Patent: Nov. 5, 2019

(54) VIBRATION SENSOR

(71) Applicant: NXP B.V., Eindhoven (NL)

(72) Inventors: Anthony Kerselaers, Herselt (BE); Liesbeth Gommé, Anderlecht (BE)

(73) Assignee: NXP B.V., Eindhoven (NL)

( * ) Notice: Subject to any disclaimer, the term of this patent is extended or adjusted under 35 U.S.C. 154(b) by 127 days.

(21) Appl. No.: 15/582,093

(22) Filed: Apr. 28, 2017

(65) Prior Publication Data
US 2018/0312166 A1    Nov. 1, 2018

(51) Int. Cl.
| | |
|---|---|
| *B60W 40/08* | (2012.01) |
| *G01N 29/42* | (2006.01) |
| *G01N 29/44* | (2006.01) |
| *G05D 1/00* | (2006.01) |
| *A61B 5/11* | (2006.01) |
| *A61B 5/16* | (2006.01) |
| *G08C 17/02* | (2006.01) |
| *A61B 5/05* | (2006.01) |
| *G01H 1/00* | (2006.01) |
| *G01H 9/00* | (2006.01) |

(Continued)

(52) U.S. Cl.
CPC .............. *B60W 40/08* (2013.01); *A61B 5/05* (2013.01); *A61B 5/11* (2013.01); *A61B 5/165* (2013.01); *G01H 1/00* (2013.01); *G01H 9/00* (2013.01); *G01N 29/42* (2013.01); *G01N 29/4454* (2013.01); *G05D 1/0088* (2013.01); *G08C 17/02* (2013.01); *A61B 5/024* (2013.01); *A61B 5/02405* (2013.01); *A61B 5/1123* (2013.01); *A61B 5/6898* (2013.01); *B60W 2040/0872* (2013.01); *B60W 2540/22* (2013.01)

(58) Field of Classification Search
CPC ......... B60W 40/08; B60W 2040/0872; B60W 2540/22; A61B 5/11; A61B 5/165; G01N 29/42; G01N 29/4454; G05D 1/0088; G08C 17/02
USPC ......................................................... 701/23
See application file for complete search history.

(56) References Cited

U.S. PATENT DOCUMENTS

| | | | |
|---|---|---|---|
| 4,683,891 A | | 8/1987 | Cornellier et al. |
| 5,776,172 A | * | 7/1998 | Schulman .......... A61N 1/36185 607/55 |

(Continued)

FOREIGN PATENT DOCUMENTS

| | | | | |
|---|---|---|---|---|
| JP | 2007209430 A | * | 8/2007 | |
| JP | 2009082362 A | * | 4/2009 | .......... A61B 5/0537 |

(Continued)

OTHER PUBLICATIONS

Wikipedia; "Magnetic particle inspection"; retrieved from the internet https://en.wikipedia.org/wiki/Magnetic_particle_inspection; 6 pages (Apr. 13, 2017).

*Primary Examiner* — Tuan C To (57) ABSTRACT

One example discloses a vibration sensor, comprising: an RF receiver circuit configured to receive an RF input signal; an RF signal characterization circuit configured to measure an attribute of the RF input signal over a set time-period; wherein the attribute of the RF input signal varies based on a physical motion between the vibration sensor and an RF source transmitting the RF input signal; and a vibration profiling circuit configured to map the attribute of the RF input signal to a vibration level.

19 Claims, 8 Drawing Sheets

(51) Int. Cl.
*A61B 5/00* (2006.01)
*A61B 5/024* (2006.01)

(56) References Cited

U.S. PATENT DOCUMENTS

| | | | | |
|---|---|---|---|---|
| 5,814,092 | A * | 9/1998 | King | A61N 1/36071 |
| | | | | 607/46 |
| 5,896,096 | A * | 4/1999 | Kim | G08B 6/00 |
| | | | | 340/407.1 |
| 6,393,325 | B1 * | 5/2002 | Mann | A61N 1/36071 |
| | | | | 607/46 |
| 9,704,154 | B2 * | 7/2017 | Xing | G06Q 20/3278 |
| 9,836,931 | B1 * | 12/2017 | Rivaud | G08B 6/00 |
| 10,104,098 | B2 * | 10/2018 | Baxley | H04W 12/08 |
| 2002/0169569 | A1 | 11/2002 | Miller | |
| 2003/0116099 | A1 * | 6/2003 | Kim | A01K 15/021 |
| | | | | 119/719 |
| 2004/0115603 | A1 * | 6/2004 | Reynolds | G09B 19/00 |
| | | | | 434/236 |
| 2009/0072768 | A1 * | 3/2009 | Murray | B06B 1/16 |
| | | | | 318/114 |
| 2010/0050259 | A1 * | 2/2010 | Christofferson | H04H 20/12 |
| | | | | 726/23 |
| 2010/0166240 | A1 * | 7/2010 | Prior | A01K 15/021 |
| | | | | 381/326 |
| 2013/0281165 | A1 * | 10/2013 | Ito | H04M 19/047 |
| | | | | 455/567 |
| 2014/0005947 | A1 | 1/2014 | Jeon et al. | |
| 2014/0070957 | A1 | 3/2014 | Longinotti-Buitoni et al. | |
| 2014/0096612 | A1 | 4/2014 | Sheikman et al. | |
| 2014/0206946 | A1 | 7/2014 | Kim et al. | |
| 2015/0033865 | A1 | 2/2015 | Rollinger | |
| 2016/0062464 | A1 * | 3/2016 | Moussette | G08B 6/00 |
| | | | | 345/173 |
| 2016/0196635 | A1 * | 7/2016 | Cho | G06T 3/40 |
| | | | | 345/660 |
| 2017/0021762 | A1 * | 1/2017 | Daman | B60Q 9/00 |
| 2017/0261406 | A1 * | 9/2017 | Dion | G01M 99/008 |
| 2018/0204426 | A1 * | 7/2018 | Nagisetty | G08B 6/00 |

FOREIGN PATENT DOCUMENTS

| | | | |
|---|---|---|---|
| JP | 2012-78331 A | | 4/2012 |
| JP | 2014183994 A | * | 10/2014 |
| WO | WO-2005092193 A1 | * | 10/2005 ........... A61B 5/1116 |

* cited by examiner

VIBRATION SENSOR

The present specification relates to systems, methods, apparatuses, devices, articles of manufacture and instructions for vibration sensing.

SUMMARY

According to an example embodiment, a vibration sensor, comprising: an RF receiver circuit configured to receive an RF input signal; an RF signal characterization circuit configured to measure an attribute of the RF input signal over a set time-period; wherein the attribute of the RF input signal varies based on a physical motion between the vibration sensor and an RF source transmitting the RF input signal; and a vibration profiling circuit configured to map the attribute of the RF input signal to a vibration level.

In another example embodiment, the attribute is at least one of: an RF input signal power level, a standard deviation (SD) of a set of RF input signal values; a number of RF input signal characteristics that exceed a threshold number in a predetermined time period; an envelope function (EF) analysis of a set of RF input signal values; or a received signal strength (RSS).

In another example embodiment, the vibration sensor is included in a biofeedback device; and variations in the vibration level indicate variations in a user stress level.

In another example embodiment, the attribute is a standard deviation (SD) of a set of RF input signal values; and the vibration profiling circuit is configured to, increase the vibration level in response to an increase in the standard deviation of the set of RF input signal values.

In another example embodiment, the attribute is a number of RF input signal characteristics that exceed a threshold number over a predetermined time period; and the vibration profiling circuit is configured to, increase the vibration level in response to an increase in the number of RF input signal characteristics that exceed the threshold number over the time period.

In another example embodiment, the RF input signal characteristic is an RF input signal power amplitude.

In another example embodiment, the attribute is an envelope function (EF) analysis of a set of RF input signal values; and the vibration profiling circuit is configured to, increase the vibration level in response to an increase in the envelope function of the set of RF input signal values.

In another example embodiment, the attribute based on a combination of a standard deviation (SD), a number of RF input signal characteristics that exceed a threshold number over a predetermined time period, and an envelope function (EF) analysis of a set of RF input signal values; and the vibration profiling circuit is configured to, increase the vibration level in response to variations in the attribute.

In another example embodiment, the RF signal characterization circuit configured to filter the attribute by removing periodicity.

In another example embodiment, the vibration sensor is embedded in a biofeedback device; and the vibration profiling circuit is configured to translate the vibration level to a relative relaxation indicator (RRI).

In another example embodiment, the vibration profiling circuit is configured to present the relative relaxation indicator either: graphically on a display; audibly on a speaker, visually as a light signal, or physically using a haptic feedback device.

In another example embodiment, the vibration sensor is configured to receive the RF input signal at an RF frequency having at least a wavelength equal to or less than a wavelength of a user's physical movements, including at least one of: walking, running, arm movements, head movements, neck movement, heartbeat movements, or other voluntary or involuntary muscle movements.

In another example embodiment, the vibration sensor is included in a vibration monitoring device; and the vibration monitoring device is configured to either, generate a mechanical resonance profile; minimize an amplitude of a mechanical resonance frequency; or maximize an amplitude of a mechanical resonance frequency.

In another example embodiment, the vibration sensor is included in an industrial or consumer device; and an increase in the vibration level beyond a threshold value either, indicates an anomalous vibration that could predict imminent failure in the industrial or consumer device; or alters an operation of the industrial or consumer device.

In another example embodiment, the vibration level is input to an optimization circuit configured to alter operation of either, a robotic device, or an autonomous vehicle.

In another example embodiment, the RF input signal is derived from at least one of: a far-field input signal, a Bluetooth input signal, or a WIFI input signal.

In another example embodiment, further comprising, a second device configured to transmit the RF input signal to the vibration sensor.

In another example embodiment, the vibration sensor is included in an autonomous vehicle system; and the autonomous vehicle system is configured to determine one or more vehicle occupant's stress level and in response alter operation of the autonomous vehicle.

In another example embodiment, the vibration profiling circuit is configured to map a set of higher vibration levels to an alert or wide-awake occupant state; and the vibration profiling circuit is configured to map a set of lower vibration levels to an impaired or drowsy occupant state.

According to an example embodiment, a wearable device, comprising: a vibration sensor, including: an RF receiver circuit configured to receive an RF input signal; an RF signal characterization circuit configured to measure an attribute of the RF input signal over a set time-period; wherein the attribute of the RF input signal varies based on a physical motion between the vibration sensor and an RF source transmitting the RF input signal; and a vibration profiling circuit configured to map the attribute of the RF input signal to a vibration level; and wherein the wearable device is at least one of: an earbud, a hearing aid, a headband, headphones, or a smartphone.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Biofeedback systems for measuring a bio parameter (e.g. heart rate variations (HRV), skin potentials, EKG brainwaves, voice stress, etc.) require significant amounts of hardware and circuitry (e.g. probe wires, accelerometers, optical sensors, half-cell potential sensors, microphones, etc.). Similarly, vibration measurement systems can have significant hardware and circuitry requirements.

Now presented is an RF vibration sensing technique which captures vibration information using radio frequency (RF) (i.e. far field) communication. Vibration information is derived from variations in an attribute of the RF signal link between an RF source transmitting the RF signal and an RF vibration sensor receiving the RF signal.

In one example, the RF vibration sensor is incorporated into a wearable device (e.g. earbuds, hearing aid, headband, headphones, smartphone, etc.) and can capture physical movements as variations in an RF signal attribute between the vibration sensor (e.g. worn or carried by a user) and the RF source (e.g. a smartphone).

From these RF signal attribute variations, a relative relaxation indicator (RRI) can be generated and presented to a user if the vibration sensor is included in a biofeedback device. The RRI can be presented to the user: on a display; via a sound, vibration, or light signal; or by some other user recognizable means, whereby the user now has additional information on and/or an awareness of stress and may then try to improve their relaxation condition.

Higher RF input signal frequencies can measure micro-movements of a user's head, neck, or other muscles with greater fidelity.

While most of the discussion that follows, describes an embodiment of the vibration sensor in a biofeedback type device, these RF vibration sensing techniques can alternatively be incorporated into various industrial and/or consumer equipment, devices or systems. Such embodiments can identify anomalous vibrations that could predict imminent mechanical failure, or help a manufacturer, or repair entity, tune the equipment, device or system for an optimal vibration level (e.g. quieter, noisier, longer-life, etc. operation).

Depending upon a distance between the RF source and the RF vibration sensor, the RF vibration sensing technique can in alternate embodiments be combined with near field communications signals as well.

This RF vibration sensing technique does not require any additional hardware, as long as a device already includes an RF receiver. Thus the RF vibration sensor can be configured to work with/or embedded in earbuds, earphones, hearing aids, etc. in a non-invasive way. In contrast, other biofeedback techniques, such as conductivity, heart rate, accelerometer based biofeedback devices, require additional hardware which burdens a user.

Wearable wireless devices which include the RF vibration sensor, may be supported by other circuits and systems, such as: a radio function, a microprocessor, a digital signal processor, an audio amplifier, a data processing unit, human interface unit, a near-field antenna, or a far field antenna.

Figure 1:
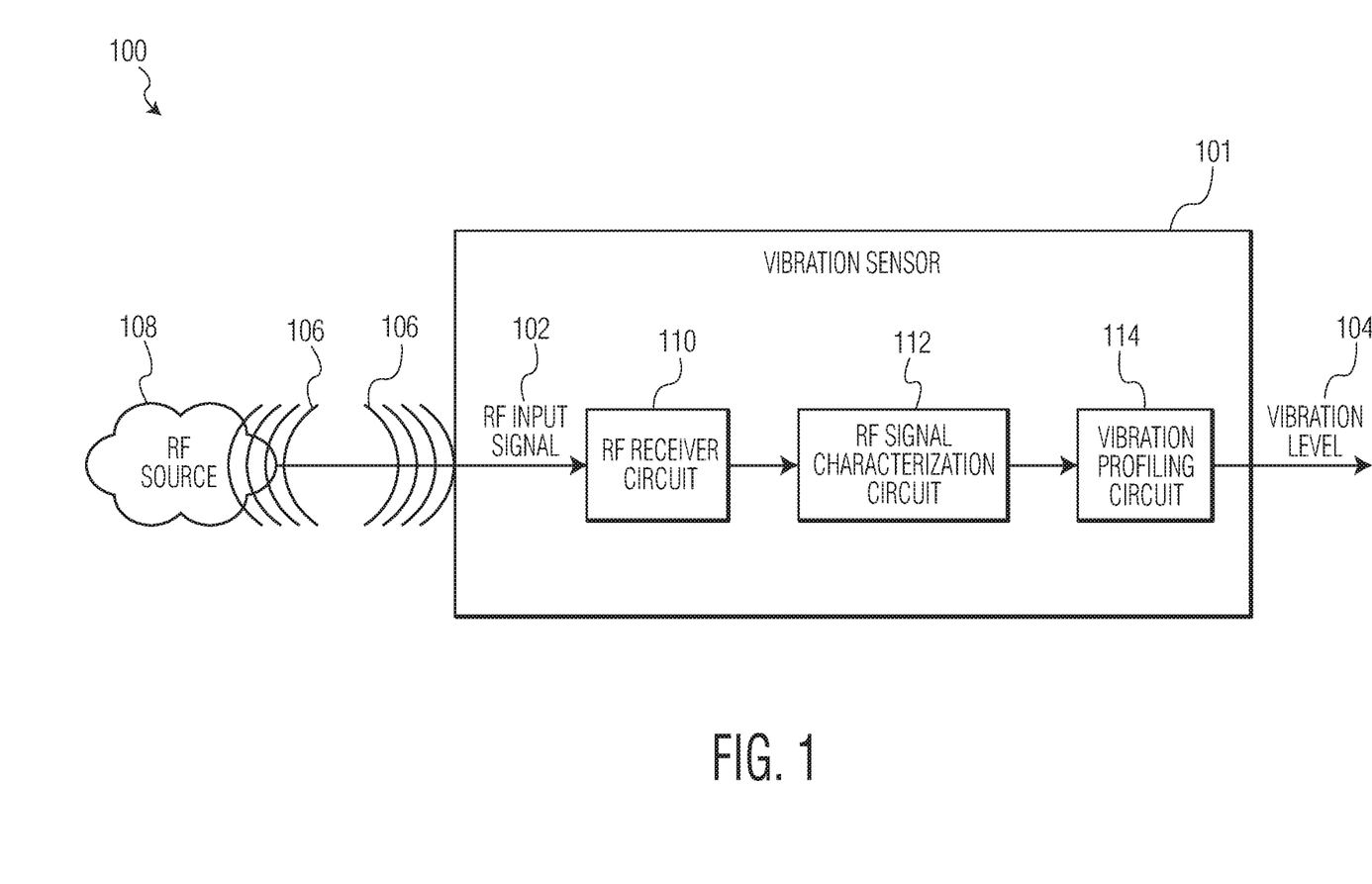
FIG. 1 is an example of vibration sensor.

FIG. 1 is an example 100 of vibration sensor 101. The example 100 shows the vibration sensor 101 coupled to receive an RF input signal 102 and output a vibration level 104. The vibration level 104 is dependent upon a physical motion 106 between the vibration sensor 101 and an RF source 108. The vibration sensor 101 includes an RF receiver circuit 110, an RF signal characterization circuit 112, and a vibration profiling circuit 114.

In one example embodiment, the RF receiver circuit 110 is configured to receive the RF input signal 102, the RF signal characterization circuit 112 is configured to measure an attribute of the RF input signal 102 over a set time-period, and the vibration profiling circuit is configured to map the attribute of the RF input signal 102 to the vibration level 104. The attribute of the RF input signal 102 varies based on the physical motion 106 between the vibration sensor 101 and the RF source 108 transmitting the RF input signal 102.

The RF input signal 102 attribute is herein defined broadly to at least include: an RF input signal power level, a standard deviation (SD) of a set of RF input signal values, an RF input signal peak-frequency (PF), an envelope function (EF) analysis of a set of RF input signal values, a received signal strength (RSS), and so on depending upon what characteristic of the RF input signal 102 is best correlated with a use-case of the vibration sensor's 101.

The attribute of the RF input signal 102 in various examples is calculated using one of the following techniques.

According a first technique, the RF input signal 102 attribute is derived from a time-varying standard deviation (SD) function of a set of RF input signal values (e.g. signal strength). The SD function is a measure that is used to quantify the amount of variation or dispersion in a set of RF input signal 102 data.

A low SD indicates that the RF input signal 102 data points tend to be close to the mean of the RF input signal 102 data set, while a high SD indicates that the RF input signal 102 data points are spread out over a wider range of values. In some example embodiments, the value of the RF input signal 102 attribute is directly given by the SD function value.

The vibration profiling circuit 114 maps the high SD to a higher vibration level 104, and the low SD to a lower vibration level 104. In a biofeedback example embodiment, a high SD indicates high physical motion of a user, and thus can be interpreted as a more stressed user.

According a second technique, the RF input signal 102 attribute is derived from a time-varying peak-frequency (PF) function of an RF input signal 102. The PF function is a measure that is used to quantify a number of RF input signal characteristics that exceed a threshold number over a pre-determined time period in the RF input signal 102 data set. In one example, the RF input signal 102 characteristic is an RF input signal 102 power amplitude.

A low PF indicates that the RF input signal 102 data points tend to be close to the mean of the RF input signal 102 set, while a high PF indicates that the RF input signal 102 data points are spread out over a wider range of values. In some example embodiments, the value of the RF input signal 102 attribute is directly given by the PF function value.

The vibration profiling circuit 114 maps the high PF to a higher vibration level 104, and the low PF to a lower vibration level 104. In a biofeedback example embodiment, a high PF indicates high physical motion of a user, and thus can be interpreted as a more stressed user.

According a third technique, the RF input signal 102 attribute is derived from a time-varying envelope function (EF) analysis of a set of RF input signal values. The EF is a measure that is used to quantify the envelope of an oscillating RF input signal 102 by outlining the signal's extreme values.

A low EF indicates that the RF input signal 102 data points tend to be stable, while a high EF indicates that the RF input signal 102 data points are spread out over a wider range of values. In some example embodiments, the value of the RF input signal 102 attribute is directly given by the EF.

The vibration profiling circuit 114 maps the high EF to a higher vibration level 104, and the low EF to a lower vibration level 104. In a biofeedback example embodiment, a high EF indicates high physical motion of a user, and thus can be interpreted as a more stressed user.

According a fourth technique, a combination of the first, second and third techniques are used to derive the RF input signal 102 attribute. With this fourth technique, non-person stress related movements recorded in the RF input signal 102 values can be eliminated. For example, a periodic fading that is created by a non-person stress related movement adds a periodicity component to the RF input signal 102 data set. Such a periodicity component can be filtered out so that only a user's stress related physical movements data are further analyzed. The filter function can be a combination of the first, second and third or other techniques.

The RF input signal 102 attribute can be output (e.g. presented to a user) in a variety of ways. For example in a biofeedback use-case, the RF input signal 102 attribute can be presented: graphically on a display; audibly on a speaker, visually using a light signal, or physically using a vibration device. However in a machine-based use-case, the RF input signal 102 attribute can be presented as one or more control signals routed to various circuits, or for controlling various apparatus/system functions.

In certain automated example embodiments, the RF input signal 102 attribute is used by an autonomous vehicle to determine one or more vehicle occupant's stress level and alter operation of the autonomous vehicle accordingly.

In one example autonomous vehicle embodiment, a measured RF input signal attribute which is higher than a first attribute threshold can be interpreted as an occupant being wide awake and alert and the autonomous vehicle secedes greater control to the driver, perhaps turning off certain automated driving functions. However, a measured RF input signal attribute which is lower than a second attribute threshold can be interpreted as an occupant being impaired (e.g. asleep, alcohol, etc.) and the autonomous vehicle take greater control, perhaps carrying the occupant home.

In another automated example embodiment, the RF input signal 102 attribute is used by an autonomous vehicle to determine one or more vehicle systems are performing anomalously, and initiate further vehicle diagnostics to maintain the vehicle's safety margins.

In other example embodiments, the RF input signal 102 attribute is incorporated into robotic systems either in an industrial setting, a retail setting, a school, or a home.

The RF input signal 102 attribute in various embodiments can be derived from either a far-field RF input signal, a Bluetooth input signal, or a WIFI signal. The Bluetooth standard may be used since this can reach out to 10 meter distance for relatively low power consumption. Bluetooth and Bluetooth low energy (BLE) use the 2.5 GHz ISM frequency band. Here far field transmission is used since the range (10 meters) is much larger than the wavelength of the transmission system 0.12 meters).

Figure 2:
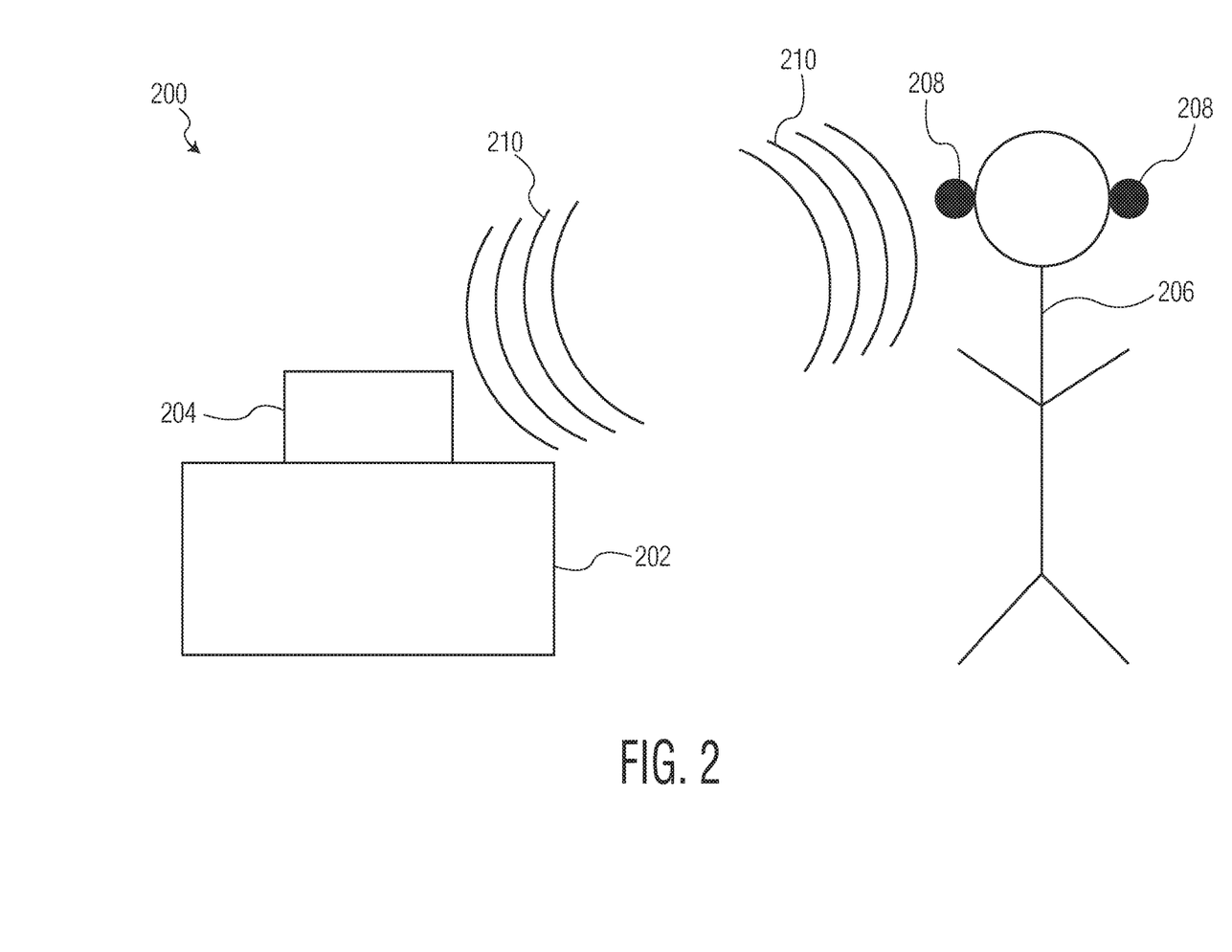
FIG. 2 is an example of the vibration sensor worn by a person walking.

FIG. 2 is an example 200 of the vibration sensor 101 worn by a person 206 walking. For example, a television 202 with a wireless transmitter 204 transmits audio to the person 206 wearing hearing aids 208.

The walking movement creates a physical motion 210 between the person 206 and the wireless transmitter 204. An RF (radio frequency) field around the person 206 varies as the person 206 walks. However if the person does not walk, but instead makes small movements with their head, the RF field will also vary.

Figure 3:
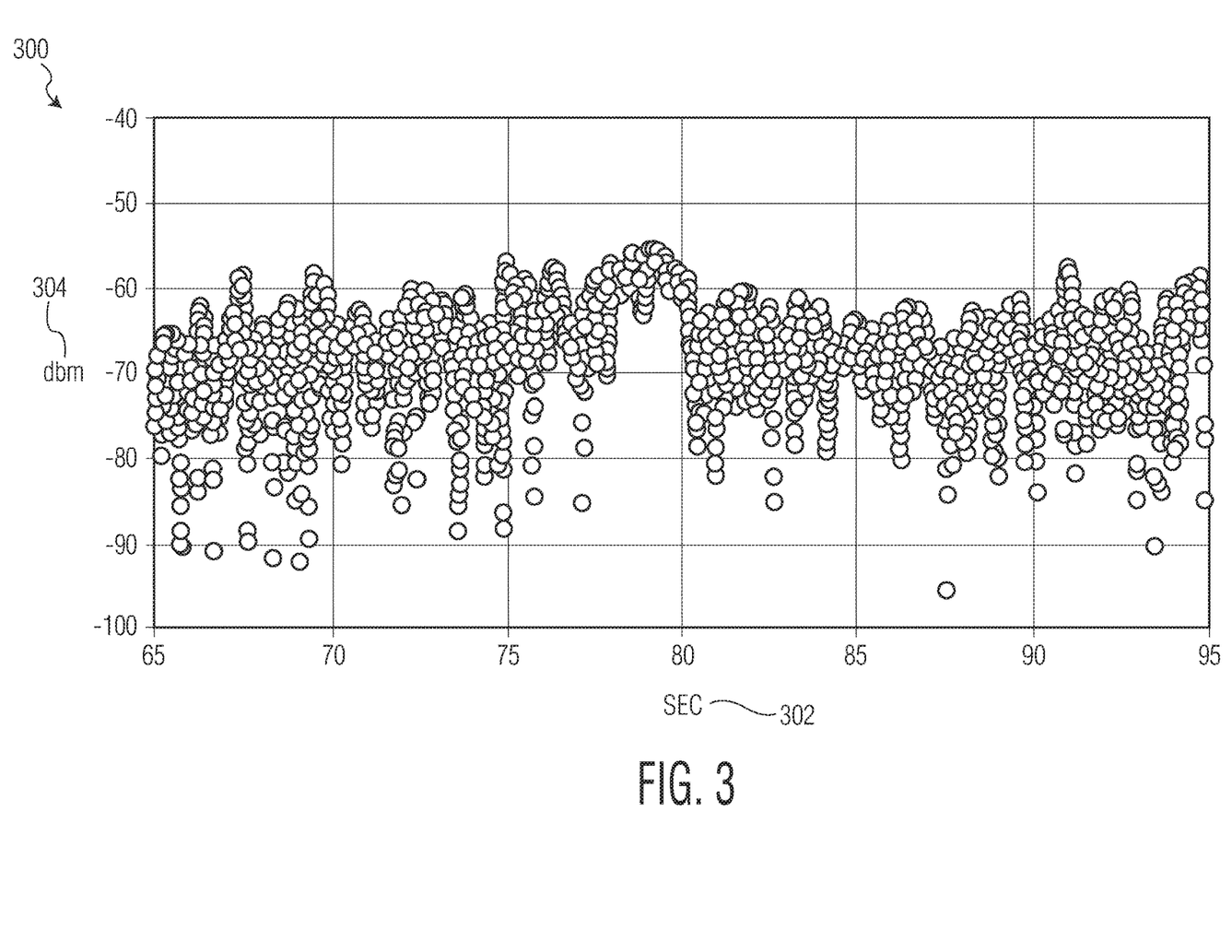
FIG. 3 is an example signal strength variation of the vibration sensor in a wearable device when the person is walking.

FIG. 3 is an example 300 signal strength variation of the vibration sensor 101 in a wearable device when the person 206 (see FIG. 2) is walking. A horizontal axis 302 is the time in seconds while a vertical axis 304 presents the RF input signal 102 power level in dbm (logarithmic power in mWatt).

The average RF input signal 102 power level is regularly diminished due to destructive reflection of the RF signals in the area, due to the line of sight and non-line of sight paths that have different lengths.

Figure 4:
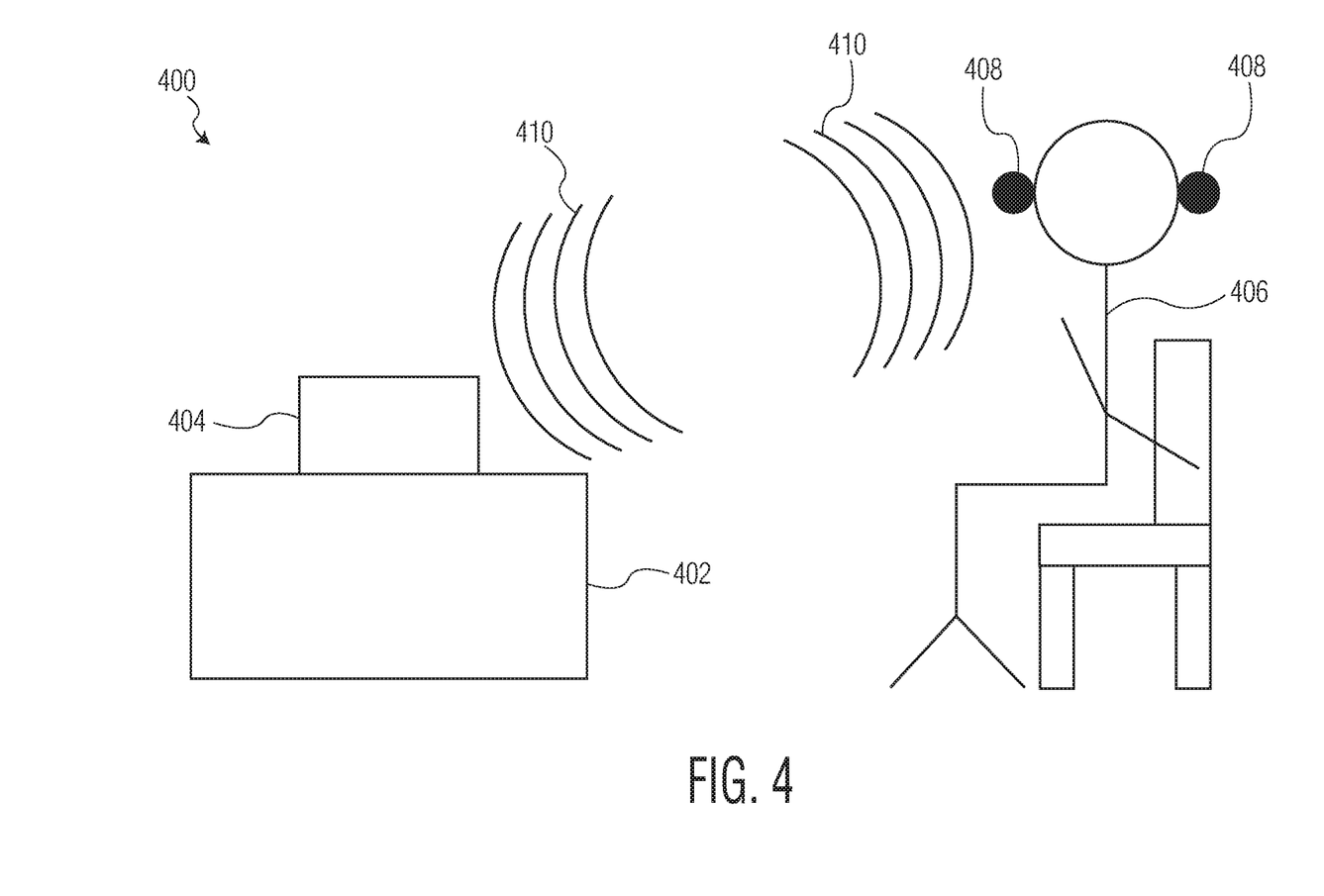
FIG. 4 is an example of the vibration sensor worn by a person sitting.

FIG. 4 is an example 400 of the vibration sensor 101 worn by a person 406 sitting. For example, a television 402 with a wireless transmitter 404 transmits audio to the person 406 wearing hearing aids 408. While the person 406 is no longer walking, micro-movements (e.g. head, neck, face, etc.) create physical motion 410 between the person 406 and the wireless transmitter 404.

The nerves of the head and neck include nerves to the most vital and important organs of the nervous system. In this region we also find the major cranial and spinal nerves that connect the central nervous system to the organs, skin, and muscles of the head and neck. These structures all work together to control every part of the person's 406 body and receive sensory messages from the body's internal structures. A less relaxed condition will result in compulsory small movements of the head which can be detected by the vibration sensor 101.

Figure 5:
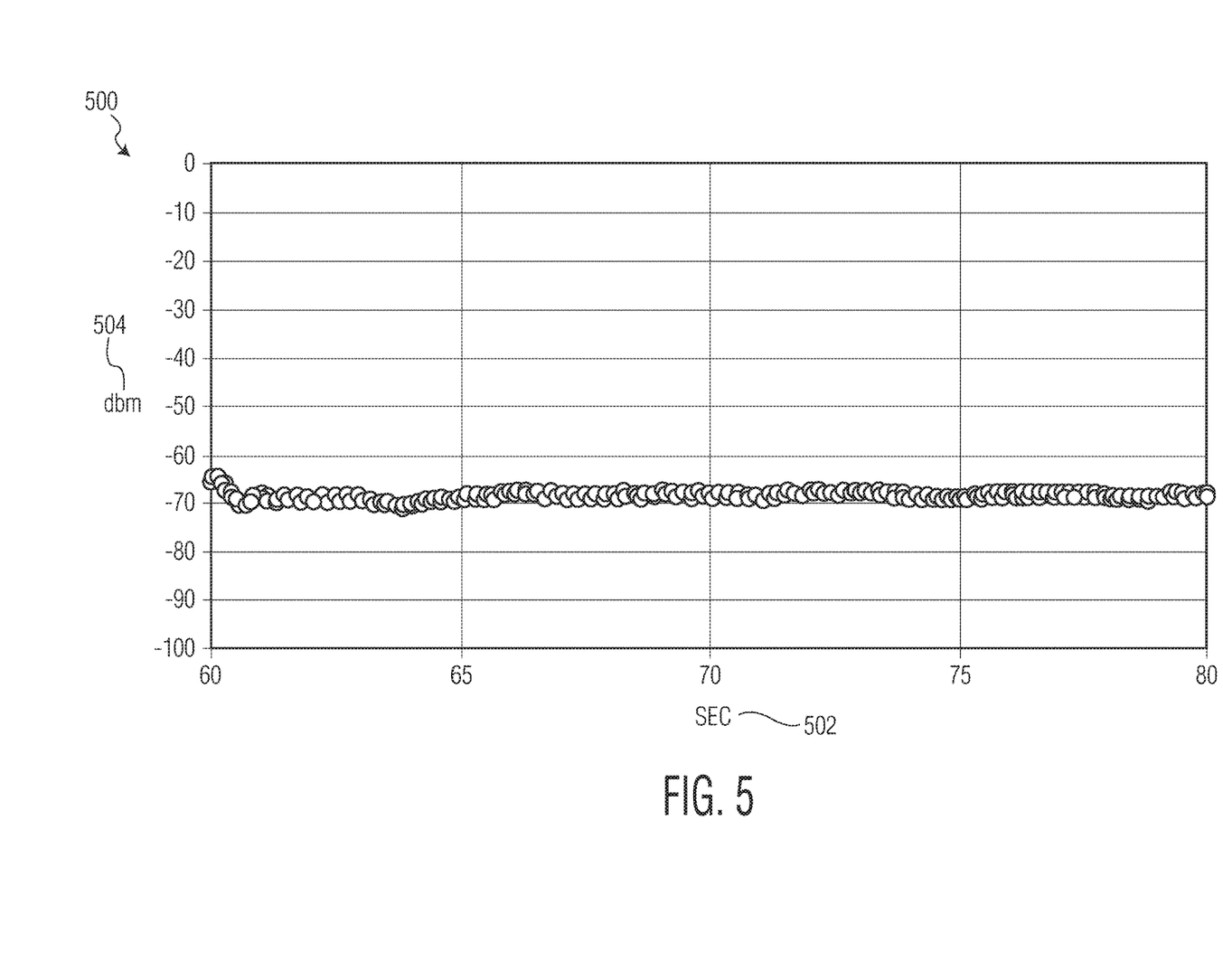
FIG. 5 is an example signal strength variation of the vibration sensor in a wearable device when the person is sitting while relaxed.

FIG. 5 is an example 500 signal strength variation of the vibration sensor 101 in a wearable device when the person 406 (see FIG. 4) is sitting while relaxed. The horizontal axis 502 is the time in seconds while the vertical axis 504 presents the RF input signal 102 power level in dbm. The average the RF input signal 102 power level is not diminished by destructive reflection of the RF signals in the area.

Since the person is very relaxed his autonomic nervous system that functions to regulate the body's unconscious actions will not result in compulsory small movements of the head and the RSS level is not diminished.

Figure 6:
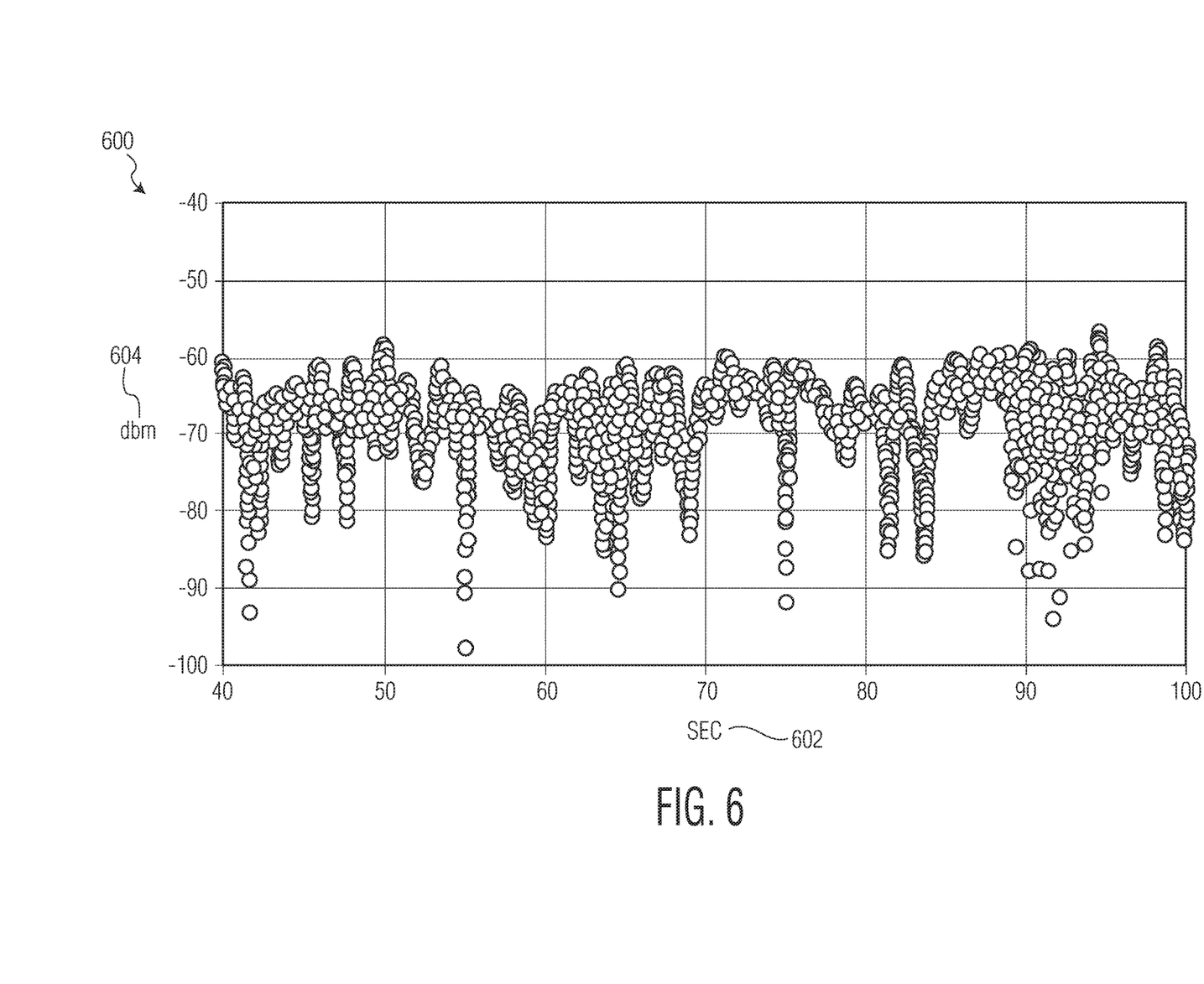
FIG. 6 is an example signal strength variation of the vibration sensor in a wearable device when the person is sitting while stressed.

FIG. 6 is an example 600 signal strength variation of the vibration sensor 101 in a wearable device when the person 406 (see FIG. 4) is sitting while stressed. The horizontal axis 602 is the time in seconds while the vertical axis 604 presents the RF input signal 102 power level in dbm. The average the RF input signal 102 power level is diminished by destructive reflection of the RF signals in the area.

Since the person is not relaxed his autonomic nervous system that functions to regulate the body's unconscious actions will result in compulsory small movements of the head and the RSS level is diminished.

Certain example embodiments of the vibration sensor 101 analyze the RF input signal 102 power level variations to distinguish between a person walking (e.g. FIG. 3), having lower-frequency major-leg-muscle-gait vibration levels, and a person sitting but under stress (e.g. FIG. 6), having higher-frequency micro-neck-muscle vibration levels. For example, RF input signal 102 variations (e.g. due to signal reflections) resulting from walking are strongly related to the dimensions of a room which the person 406 is in, while the person's 406 head movements are less strongly related to room's dimensions, since they are micromovements.

Figure 7:
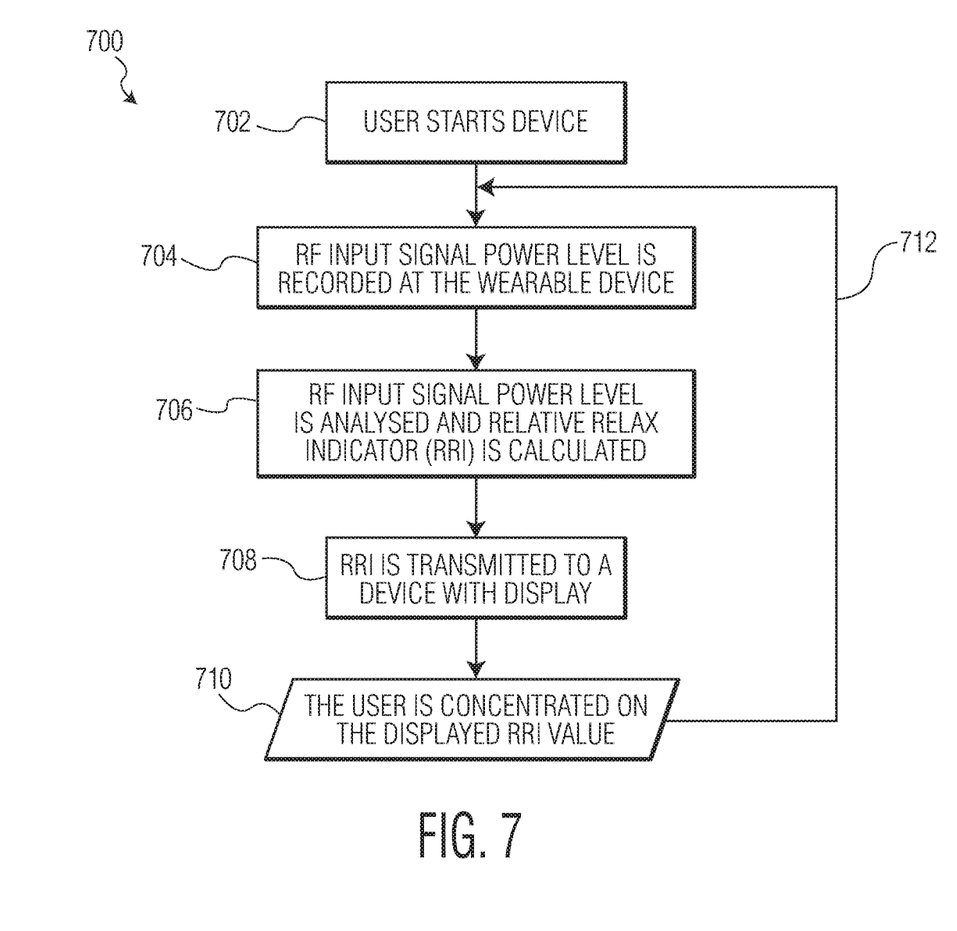
FIG. 7 is an example operating vibration sensor in a wearable biofeedback device.

FIG. 7 is an example 700 operating vibration sensor 101 in a wearable biofeedback device. In this example 700, the wearable device is in an earbud worn on a person's head. The wearable earbud receives audio from a television.

The person is sitting in a chair in a quiet environment with no other moving objects and starts the biofeedback device 702. While a sitting person will not disturb the RF input signal power level very much over time due to large-muscle movements (e.g. when walking), the person's autonomic nervous system will initiate compulsory small movements of the head, neck, etc. if the person is not otherwise relaxed.

The device begins to record the RF input signal power level 704. The relative relaxation indicator (RRI) is calculated (e.g. by the vibration profiling circuit 114 of FIG. 1) after analysis of the RF input signal power level over time 706.

The RRI can then be transmitted to the person's smartphone, or perhaps to the television as well, for display of the RRI (e.g. as a number, or in a time dependent graph) 708.

The person may then decide to concentrate on the displayed RRI and try to lower their RRI and become more relaxed 710. The person's efforts are immediately recorded by the biofeedback device and the process repeats 712. By means of this quasi real-time biofeedback approach, the person may be able to experience faster relaxation.

Figure 8:
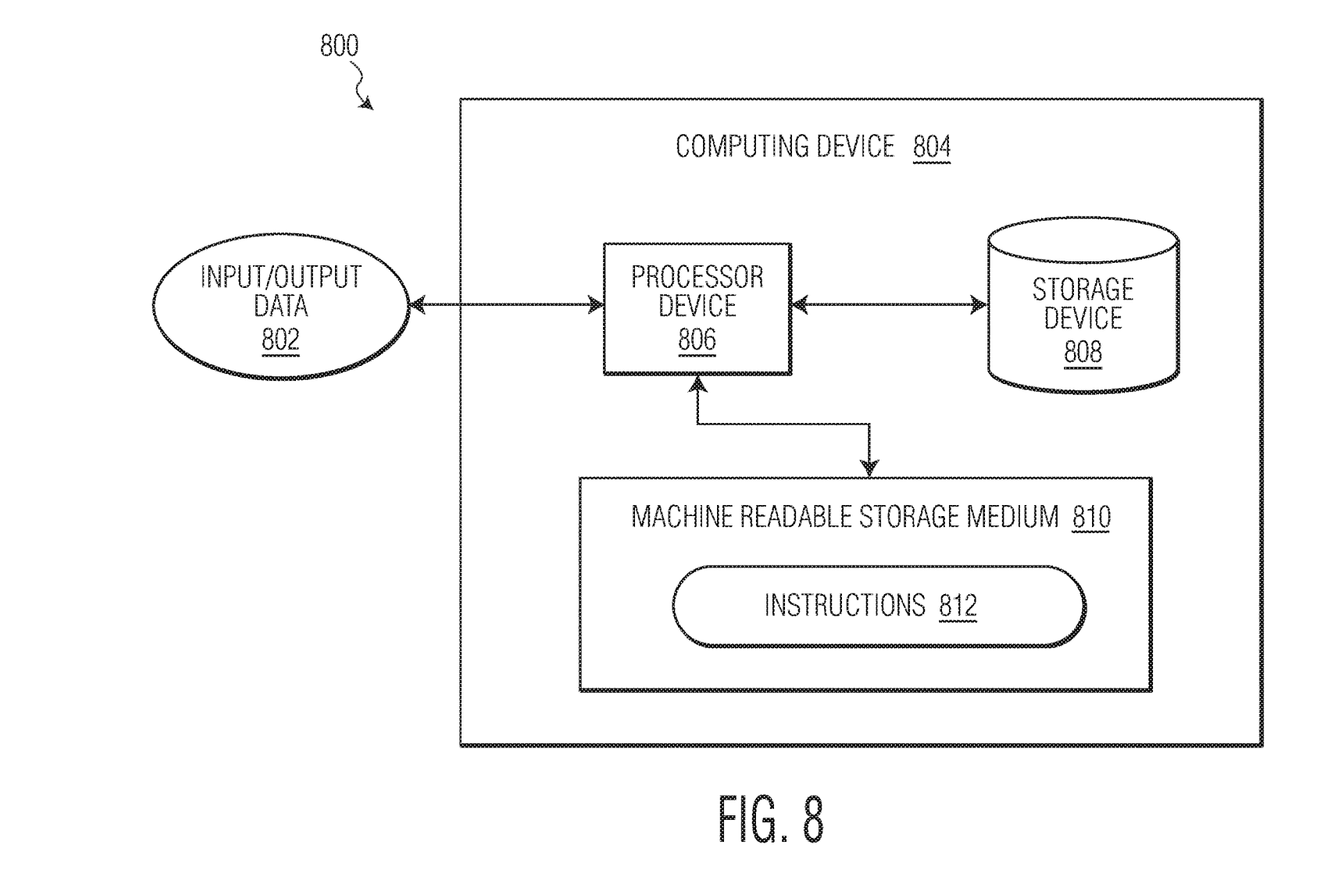
FIG. 8 is an example system for hosting instructions for enabling the vibration sensor.

FIG. 8 is example system 800 for hosting instructions for enabling the vibration sensor. The system 800 shows an input/output data 802 interface with an electronic apparatus 804. The electronic apparatus 804 includes a processor 806, a storage device 808, and a non-transient machine-readable storage medium 810. The machine-readable storage medium 810 includes instructions 812 which control how the processor 806 receives input data 802 and transforms the input data into output data 802, using data within the storage device 808. Example instructions 812 stored in the machine-readable storage medium 810 are discussed elsewhere in this specification. The machine-readable storage medium in an alternate example embodiment is a non-transient computer-readable storage medium.

The processor (such as a central processing unit, CPU, microprocessor, application-specific integrated circuit (ASIC), etc.) controls the overall operation of the storage device (such as random access memory (RAM) for temporary data storage, read only memory (ROM) for permanent data storage, firmware, flash memory, external and internal hard-disk drives, and the like). The processor device communicates with the storage device and non-transient machine-readable storage medium using a bus and performs operations and tasks that implement one or more instructions stored in the machine-readable storage medium. The machine-readable storage medium in an alternate example embodiment is a computer-readable storage medium.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A vibration sensor, comprising:
an RF receiver circuit configured to receive an RF input signal;
an RF signal characterization circuit configured to measure an attribute of the RF input signal over a set time-period;
wherein the attribute of the RF input signal varies based on a physical motion between the vibration sensor and an RF source transmitting the RF input signal; and
a vibration profiling circuit configured to map the attribute of the RF input signal to a vibration level;
wherein the attribute is a number of the RF input signal measurements that exceed a predetermined threshold over a predetermined time period; and
wherein the vibration profiling circuit is configured to, increase the vibration level in response to an increase in the number of RF input signal measurements that exceed the predetermined threshold over the predetermined time period.

2. The sensor of claim 1:
wherein the attribute is at least one of: an RF input signal power level, a standard deviation (SD) of a set of RF input signal values; a number of RF input signal characteristics that exceed a threshold number in a predetermined time period; an envelope function (EF) analysis of a set of RF input signal values; or a received signal strength (RSS).

3. The sensor of claim 1:
wherein the vibration sensor is included in a biofeedback device; and
wherein variations in the vibration level indicate variations in a user stress level.

4. The sensor of claim 1:
wherein the attribute is a standard deviation (SD) of a set of RF input signal values; and
wherein the vibration profiling circuit is configured to, increase the vibration level in response to an increase in the standard deviation of the set of RF input signal values.

5. The sensor of claim 1:
wherein the RF input signal measurement is of an RF input signal power amplitude.

6. The sensor of claim 1:
wherein the attribute is an envelope function (EF) analysis of a set of RF input signal values; and
wherein the vibration profiling circuit is configured to, increase the vibration level in response to an increase in the envelope function of the set of RF input signal values.

7. The sensor of claim 1:
wherein the attribute based on a combination of a standard deviation (SD), a number of RF input signal characteristics that exceed a threshold number over a predetermined time period, and an envelope function (EF) analysis of a set of RF input signal values; and
wherein the vibration profiling circuit is configured to, increase the vibration level in response to variations in the attribute.

8. The sensor of claim 1:
wherein the RF signal characterization circuit configured to filter the attribute by removing periodicity.

9. The sensor of claim 1:
wherein the vibration sensor is embedded in a biofeedback device; and
wherein the vibration profiling circuit is configured to translate the vibration level to a relative relaxation indicator (RRI).

10. The sensor of claim 9:
wherein the vibration profiling circuit is configured to present the relative relaxation indicator either: graphically on a display; audibly on a speaker, visually as a light signal, or physically using a haptic feedback device.

11. The sensor of claim 9:
wherein the vibration sensor is configured to receive the RF input signal at an RF frequency having at least a wavelength equal to or less than a wavelength of a user's physical movements, including at least one of: walking, running, arm movements, head movements, neck movement, heartbeat movements, or other voluntary or involuntary muscle movements.

12. The sensor of claim 1:
wherein the vibration sensor is included in an industrial or consumer device; and
wherein an increase in the vibration level beyond a threshold value either,
indicates an anomalous vibration that could predict imminent failure in the industrial or consumer device; or
alters an operation of the industrial or consumer device.

13. The sensor of claim 1:
wherein the vibration level is input to an optimization circuit configured to alter operation of either, a robotic device, or an autonomous vehicle.

14. The sensor of claim 1:
wherein the RF input signal is derived from at least one of: a far-field input signal, a Bluetooth input signal, or a WIFI input signal.

15. The sensor of claim 1:
further comprising, a second device configured to transmit the RF input signal to the vibration sensor.

16. The sensor of claim 1:
wherein the vibration sensor is included in an autonomous vehicle system; and
wherein the autonomous vehicle system is configured to determine one or more vehicle occupant's stress level and in response alter operation of the autonomous vehicle.

17. The sensor of claim 16:
wherein the vibration profiling circuit is configured to map a set of higher vibration levels to an alert or wide-awake occupant state; and
wherein the vibration profiling circuit is configured to map a set of lower vibration levels to an impaired or drowsy occupant state.

18. A wearable device, comprising:
a vibration sensor, including:
  an RF receiver circuit configured to receive an RF input signal;
  an RF signal characterization circuit configured to measure an attribute of the RF input signal over a set time-period;
  wherein the attribute of the RF input signal varies based on a physical motion between the vibration sensor and an RF source transmitting the RF input signal; and
  a vibration profiling circuit configured to map the attribute of the RF input signal to a vibration level; and
wherein the wearable device is at least one of: an earbud, a hearing aid, a headband, headphones, or a smartphone;
wherein the attribute is a number of the RF input signal measurements that exceed a predetermined threshold over a predetermined time period; and
wherein the vibration profiling circuit is configured to, increase the vibration level in response to an increase in the number of RF input signal measurements that exceed the predetermined threshold over the predetermined time period.

19. A vibration sensor, comprising:
an RF receiver circuit configured to receive an RF input signal;
an RF signal characterization circuit configured to measure an attribute of the RF input signal over a set time-period;
wherein the attribute of the RF input signal varies based on a physical motion between the vibration sensor and an RF source transmitting the RF input signal; and
a vibration profiling circuit configured to map the attribute of the RF input signal to a vibration level;
wherein the vibration sensor is embedded in a biofeedback device;

wherein the vibration profiling circuit is configured to translate the vibration level to a relative relaxation indicator (RRI); and wherein the vibration sensor is configured to receive the RF input signal at an RF frequency having at least a wavelength equal to or less than a wavelength of a user's physical movements, including at least one of: walking, running, arm movements, head movements, neck movement, heartbeat movements, or other voluntary or involuntary muscle movements.

* * * * *